United States Patent
Santerre et al.

(10) Patent No.: US 11,976,163 B2
(45) Date of Patent: May 7, 2024

(54) CARBONATE-LINKED SURFACE MODIFYING MACROMOLECULES

(71) Applicant: EVONIK CANADA INC., Burlington (CA)

(72) Inventors: J. Paul Santerre, Toronto (CA); Sanjoy Mullick, Brampton (CA)

(73) Assignee: Evonik Canada Inc., Burlington (CA)

( * ) Notice: Subject to any disclaimer, the term of this patent is extended or adjusted under 35 U.S.C. 154(b) by 893 days.

(21) Appl. No.: 16/977,964

(22) PCT Filed: Mar. 7, 2019

(86) PCT No.: PCT/CA2019/050281
§ 371 (c)(1),
(2) Date: Sep. 3, 2020

(87) PCT Pub. No.: WO2019/169500
PCT Pub. Date: Sep. 12, 2019

(65) Prior Publication Data
US 2021/0009502 A1   Jan. 14, 2021

Related U.S. Application Data

(60) Provisional application No. 62/640,839, filed on Mar. 9, 2018.

(51) Int. Cl.
| | |
|---|---|
| *C08G 64/16* | (2006.01) |
| *C07C 69/96* | (2006.01) |
| *C08F 293/00* | (2006.01) |
| *C08G 64/02* | (2006.01) |
| *C08G 64/18* | (2006.01) |
| *C08G 65/337* | (2006.01) |

(52) U.S. Cl.
CPC .......... *C08G 64/1633* (2013.01); *C07C 69/96* (2013.01); *C08F 293/00* (2013.01); *C08G 64/0233* (2013.01); *C08G 64/1666* (2013.01); *C08G 64/183* (2013.01); *C08G 64/186* (2013.01); *C08G 65/337* (2013.01)

(58) Field of Classification Search
CPC ................ C08G 64/16; C08G 64/1633; C08G 64/1666; C08G 64/183
See application file for complete search history.

(56) References Cited

U.S. PATENT DOCUMENTS

| | | | | |
|---|---|---|---|---|
| 2006/0135662 A1* | 6/2006 | Mullen | ................ | C08G 64/307 524/157 |
| 2008/0108777 A1* | 5/2008 | Davis | ................... | C08G 64/186 528/196 |

FOREIGN PATENT DOCUMENTS

| | | | |
|---|---|---|---|
| CA | 2716502 A1 | | 11/2010 |
| JP | 10-130383 A | * | 5/1998 |
| WO | 2008076345 A1 | | 6/2008 |
| WO | 2011072398 A1 | | 6/2011 |
| WO | WO 2012/073970 | * | 6/2012 |
| WO | 2016095042 A1 | | 6/2016 |

OTHER PUBLICATIONS

Machine translation of WO 2012/073970 (no date).*
PCT International Search Report and The Written Opinion of the International Searching Authority dated May 7, 2019 corresponding to PCT Application No. PCT/CA2019/050281 filed Mar. 7, 2019 (9 pages).

* cited by examiner

*Primary Examiner* — Marc S Zimmer
(74) *Attorney, Agent, or Firm* — Linda S. Li; Jason S. Ngui; Andrew H. Chung

(57) ABSTRACT

The invention relates to carbonate-linked surface modifying macromolecules and admixtures thereof. The admixtures can be used in industrial and medical applications where enhanced surface properties are desirable (e.g., surface properties reducing or preventing biofouling, immobilization of biomolecules, or denaturation of certain biomolecules).

22 Claims, 9 Drawing Sheets

YMEROH-1226-PCT-PC
MW of triol = 1,000 Da
EO = Ethylene Oxide

YMER-1226-PCT-PC
MW of diol = 1,000 Da
EO = Ethylene Oxide

XMER-1226-PCT-PC
MW of tetraol = 796 Da
EO = Ethylene Oxide
q = 4, p = 4, n = 4, m = 3

PDP-1226-PCT-PC
MW of diol = 2,000 Da
n = 8-9

C10-1226-PCT-PC
MW of diol = 2,500 Da
m ≈ 10, n ≈ 7-8

PLN-1226-PCT-PC
MW of diol = 1,900 Da
X = Z = 25, Y = 50

PLN8K-1226-PCT-PC
MW of diol = 8,000 Da
X = Z = 40, Y = 20

15PLMSi-1226-PC1-PC
MW of diol = 4,940 Da
o = 7, p = 8, x = 7, y = 8, n = 43

6PLNSi-1226-PCT-PC
MW of diol = 5,109 Da
o = 3, p = 3, x = 9, y = 9, n = 43

CARBONATE-LINKED SURFACE MODIFYING MACROMOLECULES

This Application is a 35 U.S.C. § 371 U.S. national stage of PCT International Application No. PCT/CA19/050281, filed Mar. 7, 2019, which claims the benefit of U.S. Provisional Patent Application No. 62/640,839, filed Mar. 9, 2018, the contents of each of which are hereby incorporated by reference in their entirety into this application.

FIELD OF THE INVENTION

The invention relates to surface modifying macromolecules (SMMs) and admixtures thereof with base polymers. The admixtures can be used in applications where enhanced surface properties (e.g., surface properties reducing or preventing biofouling, immobilization of biomolecules, or denaturation of certain biomolecules) are desired, e.g., in industrial and medical applications.

BACKGROUND OF THE INVENTION

Wetted surfaces can be susceptible to interaction with biological agents, such as proteins, nucleic acids, and living organisms. These interactions can lead to degradation of adsorption of the biological agent (e.g., a protein or a nucleic acid). These interactions can also lead to surface fouling by water constituents such as biomolecules, living organisms (e.g., bacteria), dissolved inorganic or organic compounds, colloids, and suspended solids. Biofouling can be attributed to accumulated extracellular materials such as soluble microbial products and extracellular polymeric substances such as polysaccharides and proteins (see, e.g., Asatekin et al., *Journal of Membrane Science*, 285:81-89, 2006). For example, membranes that are used for industrial water filtration or in medical applications (e.g., in dialysis) can suffer fouling due to, e.g., adsorption of proteins, attachment of suspended particles, or precipitated salts to the membrane. Still other examples of fouling in biomedical applications can generally result from the adherence of, e.g., cells and pathogens to the surface of a medical device (e.g., a catheter or other implantable medical devices), and such fouling can have potentially adverse outcomes. Fouling can also be evident on the hulls of marine vessels, which can become coated with marine organisms or their secretions.

Accordingly, compositions and admixtures that have surface properties of reducing or preventing biofouling, immobilization of biomolecules, or denaturation of certain biomolecules can be useful in diverse applications in industry and medicine.

SUMMARY OF THE INVENTION

The present invention features carbonate-linked surface modifying macromolecules.

In one aspect, the invention features a compound of formula (I):

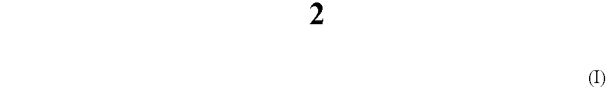

in which
(i) A comprises a soft segment and is covalently bound to B via a carbonate linkage;
(ii) B comprises a polyalkylene oxide or a moiety described by the formula:

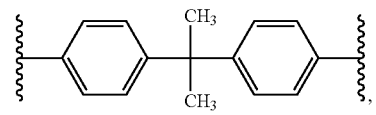

and is covalently bound to A via a carbonate linkage; and
(iii) $F_T$ is a surface active group comprising a polyfluoroorgano group, wherein $F_T$ is covalently bound to B via a carbonate linkage; and
(iv) n is an integer from 1 to 10.

In some embodiments of formula (I), the compound has a structure of formula (II):

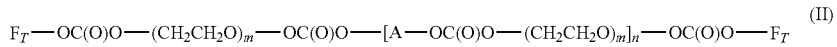

in which
(i) A comprises a soft segment;
(ii) $F_T$ is a surface active group comprising a polyfluoroorgano group;
(iii) m is an integer from 2 to 4; and
(iv) n is an integer from 1 to 10.

In formula (I), B can contain polypropylene oxide, polyethylene oxide, or polytetramethylene oxide. In formula (I), B can be formed from triethylene glycol, tetraethylene glycol, or bisphenol A.

In formula (I) or (II), A can contain hydrogenated polybutadiene (HLBH), hydrogenated polyisoprene (HHTPI), poly((2,2-dimethyl)-1,3-propylene carbonate), polybutadiene, poly(diethylene glycol)adipate (PEGA), poly(hexamethylene carbonate) (PHCN), poly(ethylene-co-butylene), (diethylene glycol-ortho phthalic anhydride) polyester, (1,6-hexanediol-ortho phthalic anhydride) polyester, (neopentyl glycol-ortho phthalic anhydride) polyester (PDP), a polysiloxane, bisphenol A ethoxylate, poly(ethylene oxide)-b-poly(propylene oxide)-b-poly(ethylene oxide) (PLN), polyethylene oxide (PEO), polypropylene oxide (PPO), or polytetramethylene oxide (PTMO).

In some embodiments of formula (I) or (II), A includes no ester linkages. For example, A includes hydrogenated polybutadiene (HLBH), hydrogenated polyisoprene (HHTPI), poly((2,2-dimethyl)-1,3-propylene carbonate), polybutadiene, poly(ethylene-co-butylene), a polysiloxane, bisphenol A ethoxylate, poly(ethylene oxide)-b-poly(propylene oxide)-b-poly(ethylene oxide) (PLN), polyethylene oxide (PEO), polypropylene oxide (PPO), or polytetramethylene oxide (PTMO).

In formula (II), A can contain a triblock copolymer PPO-b-PEO-b-(polysiloxane)-b-PEO-b-PPO (PLNSi). In formula (II), A can contain hydrogenated polyisoprene (HHTPI) or hydrogenated polybutadiene (HLBH). In formula (II), A can contain polypropylene oxide (PPO) or polytetramethylene oxide (PTMO). In formula (II), A can contain polyethylene oxide-polydimethylsiloxane-polyethylene oxide (C10 $MW_{PEO}$=2,500 Da), polyethylene oxide-polydimethylsiloxane-polyethylene oxide (C15 $MW_{PEO}$=1,000 Da), or polyethylene oxide-polydimethylsiloxane-polyethylene oxide (C22 $MW_{PEO}$=2,500 Da). In formula (II), A can contain propylene oxide-polydimethylsiloxane-propylene oxide block copolymer (C22 $MW_{PPO}$=2,500 Da). In formula (II), A can contain polyethylene oxide (PEO). In formula (II), A can contain diethylene glycol-ortho phthalic anhydride. In formula (II), A can contain poly(ethylene oxide)-b-poly(propylene oxide)-b-poly(ethylene oxide) (PLN).

In another aspect, the invention features a compound of formula (III):

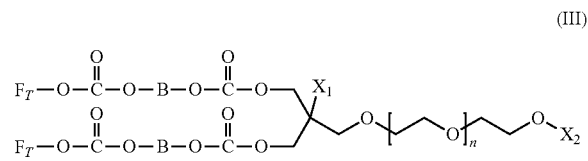

(III)

in which
(i) $F_T$ is a polyfluoroorgano group;
(ii) each of $X_1$ and $X_2$ is, independently, is H, $CH_3$, or $CH_2CH_3$;
(iii) B comprises a polyalkylene oxide; and
(v) n is an integer from 5 to 100.

In a related aspect, the invention features a compound of formula (IV):

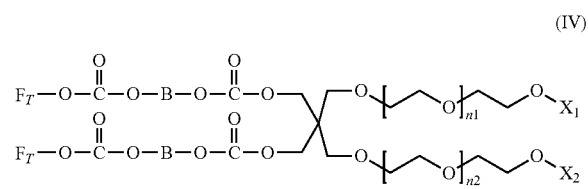

(IV)

wherein:
(i) each $F_T$ is a polyfluoroorgano;
(ii) each of $X_1$ and $X_2$ is, independently, H, $CH_3$, or $CH_2CH_3$;
(iii) B comprises a polyalkylene oxide; and
(iv) each of n1 and n2 is independently an integer from 5 to 50.

In formula (III) or (IV), B can contain polypropylene oxide, polyethylene oxide, or polytetramethylene oxide. In formula (III) or (IV), B can be formed from triethylene glycol or tetraethylene glycol. In formula (III), B can be polyethylene oxide, $X_1$ is ethyl, and $X_2$ is H (YMerOH-1226-PCT-PC). In formula (III), B can be polyethylene oxide, $X_1$ is ethyl, and $X_2$ is methyl (YMer-1226-PCT-PC). In formula (IV), B can be polyethylene oxide, $X_1$ is H, and $X_2$ is H (XMer-1226-PCT-PC).

In formula (I), (II), (III), or (IV), $F_T$ can be a radical of the general formula $CH_mF_{(3-m)}(CF_2)_rCH_2CH_2—$ and $CH_mF_{(3-m)}(CF_2)_s(CH_2CH_2O)_X—$, in which
m is 0, 1, 2, or 3;
X is an integer between 1-10;
r is an integer between 2-20; and
s is an integer between 1-20.

In some embodiments, m is 0 or 1.

In formula (I), (II), (III), or (IV), the compound can have a theoretical molecular weight of less than 10,000 Da.

Definitions

The term "alkyl," as used herein, refers to a branched or unbranched saturated hydrocarbon group, having from 1 to 10 carbon atoms ($C_{1-10}$). An alkyl may optionally include a monocyclic, bicyclic, or tricyclic ring system, in which each ring desirably has three to six members. The alkyl group may be unsubstituted or substituted with one, two, or three substituents independently selected from the group consisting of alkoxy, aryloxy, alkylthio, arylthio, halogen, disubstituted amino, and ester.

The term "alkylene," as used herein, refers to divalent alkyl groups.

The term "base polymer," as used herein, refers to a polymer having a theoretical molecular weight of greater than or equal to 20 kDa (e.g., greater than or equal to 50 kDa, greater than or equal to 75 kDa, greater than or equal to 100 kDa, greater than or equal to 150 kDa, or greater than 200 kDa). Non-limiting examples of base polymers include polyurethanes, polysulfones, polycarbonates, polyesters, polyamides, polyimides, polyalkylenes (e.g., polyethylene, polypropylene, polystyrene, polybutadiene, polyisoprene, poly(acrylonitrile-butadienestyrene), polymethylmethacrylate, polyvinylacetate, polyacrylonitrile, polyvinyl chloride), polysilicone, polysaccharides (e.g., cellulose, cellulose acetate, cellulose diacetate, or cellulose triacetate) and copolymers thereof (e.g., polyethylene terephtahate).

The term "carbonate linkage," as used herein, refers to an ester of carbonic acid.

The term "molecular weight," as used herein, refers to a theoretical weight of an Avogadro number of molecules of identical composition. As preparation of a surface modifying macromolecule can involve generation of a distribution of compounds, the term "molecular weight" refers to an idealized structure determined by the stoichiometry of the reactive ingredients. Thus, the term "molecular weight," as used herein, refers to a theoretical molecular weight.

The term "oligomeric segment," as used herein, refers to a length of a repeating unit or units that is less than about 200 monomeric units. Oligomeric segment can have a theoretical molecular weight of less than or equal to 10,000 Da, but preferably <7,000 Da and in some examples, <5,000 Da. The surface modifying macromolecule of the invention can be formed from an oligomeric segment diol, trial, or tetraol to give a compound of formula (I), (II), (III), or (IV). Non-limiting examples of oligomeric segments include polyalkylene oxide (e.g., polyethylene oxide), hydrogenated polybutadiene, hydrogenated polyisoprene, poly ((2,2-dimethyl)-1,3-propylene carbonate), polybutadiene, poly (diethylene glycol)adipate, poly (hexamethylene carbonate), poly (ethylene-co-butylene), (diethylene glycol-ortho phthalic anhydride) polyester, (1,6-hexanediol-ortho phthalic anhydride) polyester, (neopentyl glycol-ortho phthalic anhydride) polyester, a polysiloxane, and bisphenol A ethoxylate.

The term "polyalkylene," when used herein in reference to a base polymer, refers to a base polymer composed of linear or branched alkylene repeating units having from 2 to 4 carbon atoms and/or optionally a cyclic olefin of 3 to 10 carbon atoms (e.g., norbornene). Each alkylene repeating unit is optionally substituted with one substituent selected from the group consisting of chloro, methoxycarbonyl, ethoxycarbonyl, hydroxy, acetoxy, cyano, and phenyl. Polyalkylene base polymer can be a co-polymer (e.g., methymethacrylate acrylonitrile butadiene styrene (MABS), methyl methacrylate butadiene styrene (MMBS), methacrylate butadiene styrene (MBS), styrene butadiene (SB), styrene acrylonitrile (SAN), styrene methyl methacrylate (SMMA), cyclic olefin copolymers (COC), or cyclic olefin polymers (COP) copolymer). Non-limiting examples of polyalkylene base polymers include polystyrene, COP, COC, MABS, SAN, SMMA, MBS, SB, and polyacrylate (e.g., PMMA).

The term "polyether sulfone," as used herein is meant a polymer of the formula:

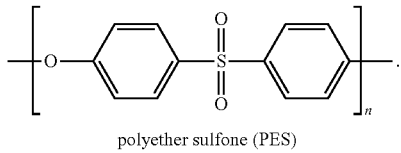

polyether sulfone (PES)

This polymer is commercially available under the trade name Radel™ from Amoco Corp.

The term "polyfluoroorgano group," as used herein, refers to a hydrocarbon group, in which from two to fifty nine hydrogen atoms were replaced with fluorine atoms. The polyfluoroorgano group contains one to thirty carbon atoms. The polyfluoroorgano group can contain linear alkyl, branched alkyl, or aryl groups, or any combination thereof. The polyfluoroorgano group can be a "polyfluoroacyl," in which the carbon atom through which the polyfluoroorgano group (e.g., polyfluoroalkyl) is attached to the rest of the molecule, is substituted with oxo. The alkyl chain within polyfluoroorgano group (e.g., polyfluoroalkyl) can be interrupted by up to nine oxygen atoms, provided that two closest oxygen atoms within polyfluoroorgano are separated by at least two carbon atoms. When the polyfluoroorgano consists of a linear or branched alkyl optionally substituted with oxo and/or optionally interrupted with oxygen atoms, as defined herein, such group can be called a polyfluoroalkyl group. Some polyfluoroorgano groups (e.g., polyfluoroalkyl) can have a theoretical molecular weight of from 100 Da to 1,500 Da. A polyfluoroalkyl can be $CF_3(CF_2)_r(CH_2CH_2)_p-$, where p is 0 or 1, r is from 2 to 20, or $CF_3(CF_2)_s(CH_2CH_2O)_X-$, where X is from 0 to 10, and s is from 1 to 20. Alternatively, polyfluoroalkyl can be $CH_mF_{(3-m)}(CF_2)_rCH_2CH_2-$ or $CH_mF_{(3-m)}(CF_2)_s(CH_2CH_2O)_X-$, where m is 0, 1, 2, or 3; X is from 0 to 10; r is an integer from 2 to 20; and s is an integer from 1 to 20. In particular embodiments, X is 0. In other embodiments, polyfluoroalkyl is perfluoroheptanoyl. In certain embodiments, polyfluoroalkyl is formed from 1H,1H,2H,2H-perfluoro-1-decanol; 1H,1H,2H,2H-perfluoro-1-octanol; 1H,1H,5H-perfluoro-1-pentanol; or 1H,1H, perfluoro-1-butanol, and mixtures thereof. In still other embodiments, polyfluoroalkyl is $(CF_3)(CF_2)_5CH_2CH_2O-$, $(CF_3)(CF_2)_7CH_2CH_2O-$, $(CF_3)(CF_2)_5CH_2CH_2O-$, $CHF_2(CF_2)_3CH_2O-$, $(CF_3)(CF_2)_2CH_2O-$, or $(CF_3)(CF_2)_5-$. In still other embodiments the polyfluoroalkyl group contains $(CF_3)(CF_2)_5-$.

By "poly(oxy-1,4-phenylene sulfonyl-1,4-phenyleneoxy-1,4-phenyleneisopropylidene-1,4-phenylene)" is meant a polymer of the formula:

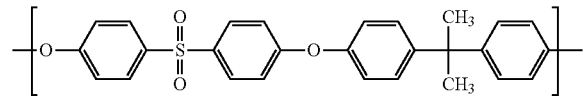

This polymer is commercially available under the trade name Udel™ P-3500 from Solvay Advanced Polymers.

As used herein, the term "polysulfone" refers to a class of polymers that include as a repeating subunit the moiety -aryl-$SO_2$-aryl-. Polysulfones include, without limitation, polyether sulfones and poly(oxy-1,4-phenylene sulfonyl-1,4-phenyleneoxy-1,4-phenyleneisopropylidene-1,4-phenylene).

By "surface active group" is meant a lipophilic group covalently tethered to a surface modifying macromolecule. The surface active group can be positioned to cap one, two, three, or four termini of the central polymeric portion of the surface modifying macromolecule. Surface active group includes polyfluoroorgano groups (e.g., polyfluoroalkyl and fluorinated polyethers), and combinations thereof.

The term "surface modifying macromolecule," as used herein, refers to the macromolecules described herein (e.g., a compound according to any one of formulas (I)-(IV), e.g., a compound of any one of compounds (1)-(9)).

The term "thermal degradation temperature," as used herein, refers to the lowest temperature at which there is an onset of weight loss of at least 5% (w/w) of the surface modifying macromolecule during thermogravimetric analysis.

Other features and advantages of the invention will be apparent from the Drawings, Detailed Description, and the claims.

DETAILED DESCRIPTION

Figure 1:
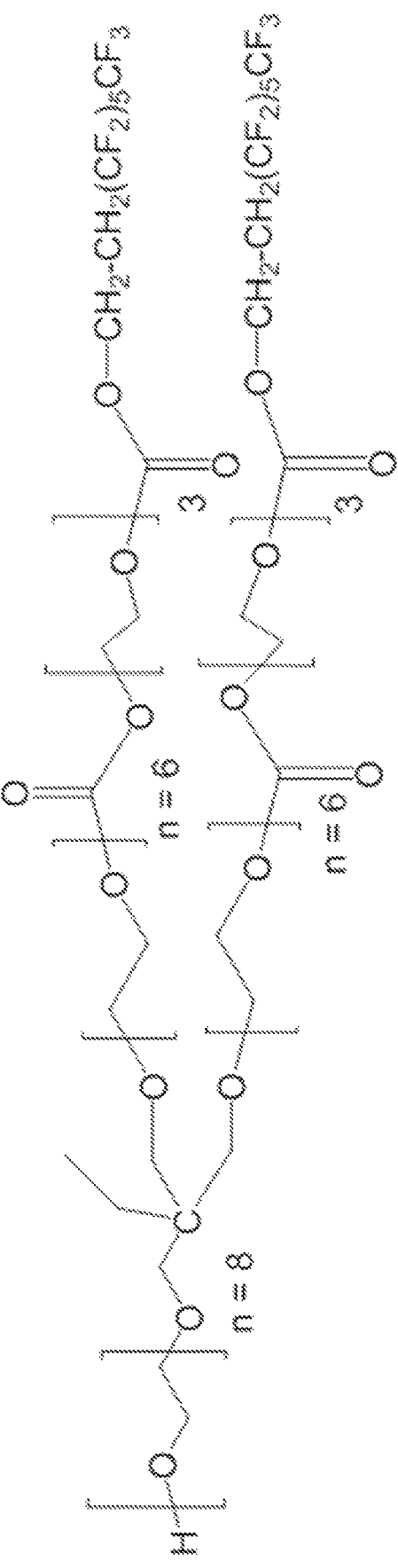
FIG. 1 shows the structure of compound (1).

In general, the present invention provides surface modifying macromolecules (SMMs), the structure of which is based on linking an oligomeric segment to a surface active group through a linker having at least one carbonate bond. The surface modifying macromolecule of the invention can have a structure of any one of formulae (I)-(IV) described herein (e.g., the surface modifying macromolecule of the invention can be any one of compounds (1)-(9)).

The present invention provides carbonate linkers that can introduce hydrophilic surface energetics in base polymers despite migration of the highly hydrophobic fluoroalkyl end groups to the surface but undergo rearrangements to expose the hydrophilic ethylene oxide groups present in the carbonate linkers.

Typically, urethanes are H-donors that tend to aggregate together due to self H-bonding. As a result, such urethanes can have high contact angles, being predominantly hydrophobic, and pose challenges in interacting with water, which is an important criterion for the use of SMMs to impart anti-biofouling properties to a surface. In contrast, the present invention describes hydrophilic compounds that include polyethylene oxide units in combination with carbonate linkages (e.g., FIG. 1). The hydrophilic character of the carbonate-linked SMMs can be important as they attract water, and provide anti-biofouling characteristics, as compared to traditional polyurethanes.

The compounds of the invention can be hydrolytically stable in comparison to the corresponding compound in which the carbonate linkage is replaced by ester linkages.

In particular, the invention provides admixtures of base polymers with surface modifying macromolecules and articles made therefrom. In some embodiments, more than one SMM including carbonate is used in admixtures with the base polymer. The articles of the invention can exhibit advantageous surface properties relative to the articles lacking a surface modifying macromolecule. For example, the surface properties can be modified to render such a surface resistant to biofouling, immobilization of biomolecules, or mediation of biomolecule denaturation. Biofouling can be attributed to accumulated extracellular materials, such as soluble microbial products and extracellular polymeric substances, e.g., polysaccharides and proteins (e.g., Asatekin et al., Journal of Membrane Science, 285:81-89, 2006). In particular, the surfaces of the invention can be resistant to fouling (e.g., biofouling). The surface of the invention can also reduce degradation (e.g., through adsorption or denaturation) of a biological agent (e.g., a polypeptide (e.g., a monoclonal antibody or an antigen-binding fragment thereof), a polynucleotide (e.g., siRNA or an antisense compound), or a vaccine); the degradation can be due to interactions between the biological agent and a surface lacking a surface modifying macromolecule. Without being bound by a theory, the inclusion of the surface modifying macromolecule can alter the surface wetting (with water), thereby reducing the contact between a biological agent (e.g., a protein, a nucleic acid, or bacteria) and the surface. The surface of the invention may be capable of sustaining a prolonged contact with a biologic without causing substantial denaturation or immobilization, e.g., the biologic can be abatacept, interferon β-1a, or insulin. In particular, these and other biologics may benefit from the surface properties of the invention, the surface properties reducing or preventing undesired interactions between the surface and the biologic (e.g., immobilization and/or denaturation of the biologic). Alternatively, the inclusion of the surface modifying macromolecule can increase the surface wetting (with water). Such materials may be useful in applications requiring a hydrophilic surface.

The desired surface properties in the articles of the invention are believed to be provided by surface modifying macromolecules of the invention that migrate during manufacturing to the surface of the article, thereby exposing the surface active groups at the surface of the article. The surface active groups are likely responsible, in part, for carrying the surface modifying macromolecule to the surface of the admixture, where the surface active groups are exposed on the surface. The migration of the surface modifying macromolecules to the surface is a dynamic process and is dependent on the surface environment. The process of migration is driven by the tendency towards establishing a low surface energy at the mixture's surface. When the balance between anchoring and surface migration is achieved, the surface modifying macromolecule remains stable at the surface of the polymer, while simultaneously altering surface properties. Anchoring within the base polymer can be provided by the oligomeric segment.

Aggregation of multiple oligomeric molecules can increase their effective molecular radius, thereby lowering the permeability of the oligomeric molecules through a base polymer. Efficacy of the surface properties modification can be improved by the surface modifying macromolecules of the invention. By excluding the combinations of hydrogen-bond donors and acceptors within the same molecule, the ability of the surface modifying macromolecules of the invention to migrate to the surface of an article can be enhanced due to the likely reduction in aggregation. In addition, SMMs which include carbonate bonds may exhibit increased stability as compared to SMMs with ester bonds due to a greater stability to hydrolytic degradation of the carbonate bond. The surface modifying macromolecules of the invention can exhibit enhanced ability to migrate to the surface of an article without compromising their anchoring in a base polymer. Thus, certain of the surface modifying macromolecules of the invention do not contain hydrogen bond donors (e.g., O—H, N—H, or S—H moieties). In particular, the surface modifying macromolecules may be free of urethane moieties.

The selection of the combination of a particular SMM and a particular base polymer can be determined by a number of factors. First, the type and amount of SMM to be added to base polymer is determined in part by whether the admixture forms a single stable phase, where the SMM is soluble in the base polymer (e.g., separation of the admixture to form two or more distinct phases would indicate an unstable solution). Then, the compatibility of the admixture can be tested by various known analytical methods. The surface of the admixture as a film or as a fiber can be analyzed by any useful spectroscopic method, such as X-ray photoelectron spectroscopy (XPS) with an elemental analysis (EA). Data from XPS could indicate the extent of modification of the surface by migrating SMMs and data from EA can indicate the extent of modification of the bulk material. Stable admixtures can then be tested to determine the antifouling properties of the surface under various conditions.

In particular embodiments, the surface modification can maintain transparency relative to a neat base polymer. Often the inclusion of admixtures in a base polymer can result in diminished optical properties (e.g., lower transparency), thereby limiting the utility of such materials in applications, where transparency of the material is desirable. In contrast, the articles of the invention including a surface modifying macromolecule and a base polymer can have the transparency that is the same or slightly lower than that of the neat base polymer.

Articles of the invention can be prepared, at least in part, from a base polymer using a process requiring a high temperature processing (e.g., extrusion or molding). For example, COC and COP often require processing temperatures of greater than 200° C. (e.g., greater than or equal to 250° C., or greater than or equal to 300° C.). Some compounds of the invention, e.g., PDP-1226 PCT (Tg=314° C.), are appropriate for high temperature processing. The surface modifying macromolecules described herein can be thermally stable (e.g., can have a thermal degradation temperature of greater than or equal to 200° C. (e.g., greater than or equal to 250° C. or greater than or equal to 300° C.). Accordingly, articles of the invention can be formed from an admixture of a base polymer and a surface modifying macromolecule at a temperature of greater than 200° C. (e.g., greater than or equal to 250° C. or greater than or equal to 300° C.). Articles of the invention can be manufactured (e.g., through high temperature processing, such as melt processing) from an admixture of a base polymer and a surface modifying macromolecule. The surface modifying macromolecule can be added prior to melt processing of the base polymer to produce an article of the invention. To form an admixture by melt processing, the surface modifying macromolecule can be, for example, mixed with pelletized or powdered polymer and then melt processed by known methods such as, for example, molding or melt extrusion. The surface modifying macromolecule can be mixed directly with the polymer in the melt condition or can first be pre-mixed with the polymer in the form of a concentrate of the surface modifying macromolecule/polymer admixture in a brabender mixer. If desired, an organic solution of the surface modifying macromolecule can be mixed with powdered or pelletized base polymer, followed by evaporation of the solvent and then by melt processing. Alternatively, the surface modifying macromolecule can be injected into a molten polymer stream to form an admixture immediately prior to extrusion into the desired shape.

After melt processing, an annealing step can be carried out to enhance the development of advantageous properties described herein in the base polymer. In addition to, or in lieu of, an annealing step, the melt processed combination can also be embossed between two heated rolls, one or both of which can be patterned. An annealing step typically is conducted below the melt temperature of the polymer (e.g., at from about 50° C. to about 220° C.).

The surface modifying macromolecule is added to a base polymer in amounts sufficient to achieve the desired surface properties for a particular application. Typically, the amount of surface modifying macromolecule used is in the range of 0.05-15% (w/w) of the admixture. The amounts can be determined empirically and can be adjusted, as necessary or desired, to achieve the desired surface properties without compromising other physical properties of the base polymer.

Surface Modifying Macromolecules

Surface modifying macromolecules of the invention can be compounds of any one of formulae (I), (II), (III), and (IV).

The surface modifying macromolecule of the invention can be a compound of formula (I):

$$F_T\text{—OC(O)O—B—OC(O)O—[A—OC(O)O—B]}_n\text{—OC(O)O—}F_T, \quad (I)$$

in which

A comprises a soft segment and is covalently bound to B via a carbonate linkage;

B comprises a polyalkylene oxide or a moiety described by the formula:

[structure: two para-phenylene groups connected by a C(CH$_3$)$_2$ group]

and is covalently bound to A via a carbonate linkage; and $F_T$ is a surface active group comprising a polyfluoroorgano group, where $F_T$ is covalently bound to B via a carbonate linkage; and n is an integer from 1 to 10.

In particular, a compound of formula (I) can be a compound of formula (II):

$$F_T\text{—OC(O)O—(CH}_2\text{CH}_2\text{O)}_m\text{—OC(O)O—[A—OC(O)O—(CH}_2\text{CH}_2\text{O)}_m]_n\text{—OC(O)O—}F_T, \quad (II)$$

in which

A comprises a soft segment;

$F_T$ is a surface active group comprising a polyfluoroorgano group;

m is an integer from 2 to 4; and n is an integer from 1 to 10.

The surface modifying macromolecule of the invention can be a compound of formula (III):

(III)

[structure showing:
$F_T$—O—C(O)—O—B—O—C(O)—O—
$F_T$—O—C(O)—O—B—O—C(O)—O—
both connecting to a central carbon bearing $X_1$ and —O—(CH$_2$CH$_2$O)$_n$—$X_2$]

in which $F_T$ is a polyfluoroorgano group;

each of $X_1$ and $X_2$ is, independently, is H, CH$_3$, or CH$_2$CH$_3$;

B comprises a polyalkylene oxide; and n is an integer from 5 to 100.

The surface modifying macromolecule of the invention can be a compound of formula (IV):

(IV)

[structure showing:
$F_T$—O—C(O)—O—B—O—C(O)—O—
$F_T$—O—C(O)—O—B—O—C(O)—O—
connecting to a central carbon with two branches: —O—(CH$_2$CH$_2$O)$_{n1}$—$X_1$ and —O—(CH$_2$CH$_2$O)$_{n2}$—$X_2$]

in which each $F_T$ is a polyfluoroorgano;

each of $X_1$ and $X_2$ is, independently, H, CH$_3$, or CH$_2$CH$_3$;

B comprises a polyalkylene oxide; and each of n1 and n2 is independently an integer from 5 to 50.

Oligomeric Segments

The surface modifying macromolecules of the invention can be prepared from an oligomeric segment diol, triol, or tetraol. Because the reactions are moisture sensitive, they are typically carried out under an inert N$_2$ atmosphere and under anhydrous conditions. The resulting surface modifying macromolecules can be isolated and purified as appropriate. Surface modifying macromolecules of formula (III) or (IV) can be prepared, for example, from commercially available mono-dihydroxysubstituted-alkyl or alkyloxyalkyl-terminated PEGs (e.g., Ymer™ N120, a difunctional polyethylene glycol monomethyl ether, from Perstorp). Exemplary oligomeric segment diols, triols, and tetraols are shown below.

Scheme 1 shows a non-limiting example of a structure of an oligomeric segment triol that can be used to prepare a surface modifying macromolecule of formula (III):

Scheme 1

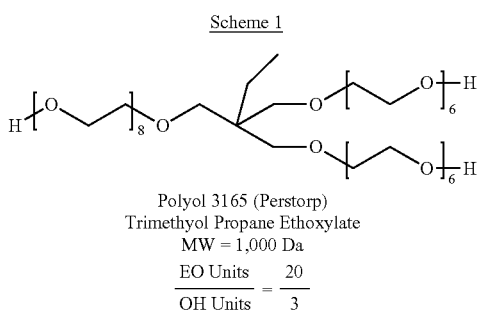

Polyol 3165 (Perstorp)
Trimethyol Propane Ethoxylate
MW = 1,000 Da
$$\frac{\text{EO Units}}{\text{OH Units}} = \frac{20}{3}$$

Scheme 2 shows some of the oligomeric segment diols that can be used in the preparation of compounds of formulas (I) or (II):

Scheme 2

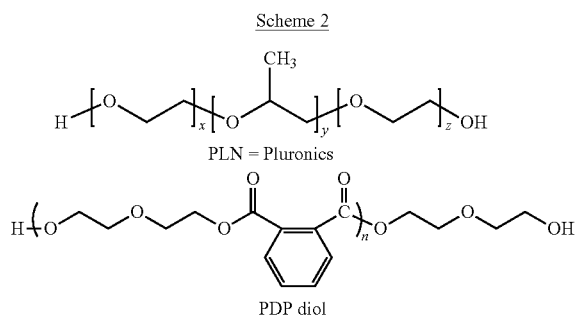

PLN = Pluronics

PDP diol

Scheme 3 shows some of the oligomeric segment diols that can be used in the preparation of compounds of formula (II):

Diols known in the art can be used to prepare the compound of formula (I) or (II). For example, the diol of an oligomeric segment can be selected from the group consisting of polyurea, polyurethane, polyamide, polyalkylene oxide, polycarbonate, polyester, polylactone, polysilicone, polyether sulfone, polyalkylene, polyvinyl, polypeptide polysaccharide, or an ether-linked or amine-linked segments thereof (e.g., the segment in this case can refer to a repeating unit in the listed oligomer).

Synthesis

The compounds of the invention can be prepared using methods analogous to those described in the Examples starting from the appropriately selected reagents, such as dicarboxylic acid derivatives, diols, and fluorinated alcohols to form a wide range of carbonate-based surface modifying macromolecules.

Articles

The invention further features an article formed from an admixture of the invention. Articles that can be formed using the admixtures of the invention include, without limitation, surgical caps, surgical sheets, surgical covering clothes, surgical gowns, masks, gloves, surgical drapes, filter (e.g., part of a respirator, water filter, air filter, or face mask), cables, films, panels, pipes, fibers, sheets, and implantable medical device (e.g., a cardiac-assist device, a catheter, a stent, a prosthetic implant, an artificial sphincter, or a drug delivery device).

The surface modifiers and admixtures of the invention can be used in films and nonwoven applications, e.g., surgical drapes, gowns, face masks, wraps, bandages, and other protective wear garments for medical technicians (e.g., workers overalls, labcoats) require high temperature processing often exceeding 200° C. in the form of extruded articles (e.g., thermoplastic films, thermoplastic fibers, fibrous nonwoven materials, thermoplastic foam materials,

Scheme 3

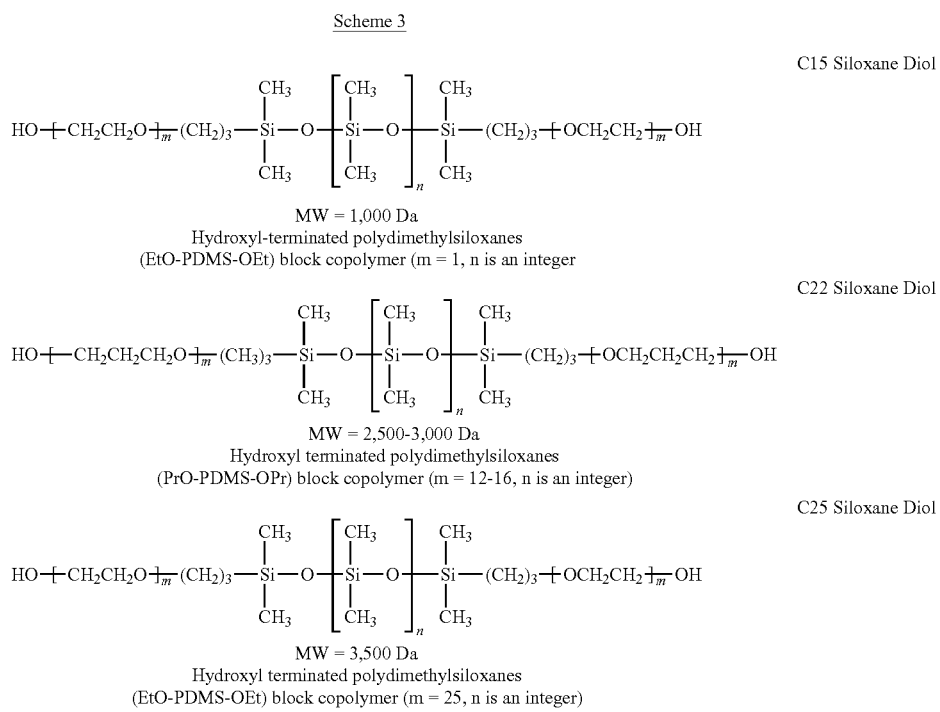

etc.) where processing temperatures can reach a range of 250-300° C. In particular embodiments, the surface modifiers used in the nonwoven application are formed from bisphenol A. The surface modifiers and admixtures of the invention can also be used in implantable medical devices (e.g., central venous catheters to impart reduced occlusion properties, and increased blood compatibility). The surface modifiers and admixtures of the invention may also be used in hollow fiber membrane filtration made from polyethylene, polypropylenes, or polysiloxane base polymers for fluid or gas separation.

The surface modifiers and admixtures of the invention can have the required high temperature stability during the processing in nonwoven fabric manufacturing or the compatibility with the polymers that are used in catheter manufacture. The admixtures of the invention can have the required high temperature stability during the processing. In particular embodiments, the surface modifiers suitable for high temperature processing are formed from bisphenol A. The admixtures therefore can provide the required resistance to degradation at high temperatures while providing the desired biocompatible properties, such as resistance to biofouling, resistance to immobilization of biomolecules on the surface, and resistance to mediation of biomolecule denaturation. The technology can involve the incorporation of the SMMs into the base polymers which then bloom to the surface, thus modifying the surface of the polymers but keeping the bulk properties intact. The base polymers now have a fluorinated surface with a high degree of hydrophobicity. Articles that may be formed from the admixtures of the invention include implanted medical devices which can be percutaneous or cutaneous.

Implanted Devices

Devices that may be formed from the admixtures of the invention include implanted devices. Implanted devices include, without limitation, prostheses such as pacemakers, electrical leads such as pacing leads, defibrillators, artificial hearts, ventricular assist devices, anatomical reconstruction prostheses such as breast implants, artificial heart valves, heart valve stents, pericardial patches, surgical patches, coronary stents, vascular grafts, vascular and structural stents, vascular or cardiovascular shunts, biological conduits, pledges, sutures, annuloplasty rings, stents, staples, valved grafts, dermal grafts for wound healing, orthopedic spinal implants, orthopedic pins, intrauterine devices, urinary stents, maxial facial reconstruction plating, dental implants, intraocular lenses, clips, sternal wires, bone, skin, ligaments, tendons, and combination thereof. Percutaneous devices include, without limitation, catheters of various types, cannulas, drainage tubes such as chest tubes, surgical instruments such as forceps, retractors, needles, and gloves, and catheter cuffs. Cutaneous devices include, without limitation, burn dressings, wound dressings and dental hardware, such as bridge supports and bracing components.

Exemplary uses of the medical devices modified with SMMs as described herein include use as biosensors, catheters, heart valves, orthopedic implants, ureteral stents, ventilation tubes, and drug-delivery devices. In a particular embodiment, admixtures that include a surface modifier that includes a polysiloxane as a soft segment are used in the manufacture of catheters.

EXAMPLES

Abbreviations

YMer (diol)=hydroxy-terminated polyethylene glycol monomethyl ether

YMerOH (triol)=trimethylolpropane ethoxylate
YMer™=polyethylene glycol monomethyl ether diol
XMer (tetraol)=pentaerythritol ethoxylate
C10 (diol)=hydroxyl-terminated polydimethylsiloxane (ethylene oxide-PDMS-ethylene oxide) block copolymer (C10 MW$_{PEO}$=2,500 Da)
C25 (diol)=hydroxy-terminated polidimethylsiloxane (ethylene oxide-PDMS-ethylene oxide) block copolymer (C25 MW$_{PEO}$=3,500 Da)
PLN8K (diol)=pluronic type (polyethylene oxide-block-polypropylene oxide-block-polyethylene oxide), PEO:PPO=80:20
PLN (diol)=pluronic type (polyethylene oxide-block-polypropylene oxide-block-polyethylene oxide), PEO:PPO=50:50
6PLNSi (diol)=hydroxyl-terminated pluronic type polydimethylsiloxane (PPO-PEO-Si-PEO-PPO) block copolymer, PEO:PPO=75:25
16PLNSi (diol)=hydroxyl-terminated pluronic type polydimethylsiloxane (PPO-PEO-Si-PEO-PPO) block copolymer, PEO:PPO=50:50
PDP=linear diethylene glycol-ortho phthalic anhydride diol
PEGA=poly(di(ethylene glycol adipate))diol
MABS=methymethacrylate acrylonitrile butadiene styrene
MMBS=methyl methacrylate butadiene styrene
MBS=methacrylate butadiene styrene
SB=styrene butadiene
SAN=styrene acrylonitrile
SMMA=styrene methyl methacrylate Preparation of Surface Modifying Macromolecules General Synthesis Description for Carbonate-Based Surface Modifying Macromolecules The compounds of the invention can be synthesized, for example, by reacting a TEG bis chlorformate with Capstone 62-AL fluoroalcohol to give a partially fluorinated TEG bis chlorformate-Capstone 62-AL intermediate, which is then reacted with a soft segment diol, triol, or tetraol to give the desired product. In addition, the compounds of the invention can be synthesized, for example, by reacting a soft segment diol with bisphenol A chlorformate to give a diol-bisphenol A intermediate, which is then reacted with Capstone 62-AL fluoroalcohol to give the desired product. Further details are provided below.

Synthesis of Compound 1

All glassware used for the synthesis was dried in an oven at 110° C. overnight.

20 g (0.020 mol) of YMerOH triol (MW=1000 Da) was added to a 200 mL 2-neck flask which was degassed overnight then purged with N$_2$. To a 500 mL 2-neck oven-dried flask equipped with a stir bar was added 21.70 g (0.079 mol) triethylene glycol (TEG) bis chlorformate. The flask was degassed for 15 min and then purged with dry N$_2$. After purging, 62 mL of anhydrous toluene were transferred into the flask by means of a cannula. The TEG bis chlorformate was stirred to dissolve in the solvent. This is now cooled under an ice bath for 15 min. To a 50 mL addition funnel was added 28.73 g (0.079 mol) of Capstone 62-AL fluoroalcohol (1H,1H,2H,2H-perfluoro-1-octanol), then degassed for 15 min and purged with dry N$_2$. To this addition funnel were added 21 mL of anhydrous toluene, followed by 7 g of anhydrous pyridine, and the funnel was shaken to dissolve all reagents. The addition funnel was attached to the reaction flask and a dropwise addition of Capstone 62-AL to the cooled solution of TEG bis chlorformate was started. During addition the stirring was kept to a minimum. The reaction was allowed to proceed for additional 10 min after addition was completed at room temperature (25° C.) under $N_2$ atmosphere to form a partially fluorinated TEG bis chloroformate-Capstone 62-AL intermediate. While the partial fluorination was in progress, anhydrous toluene (125 mL) was added to the flask containing the YMerOH triol via a cannula followed by 6 g of anhydrous pyridine and the mixture was stirred to dissolve the YMerOH triol. A 250 mL addition funnel was attached to the 500 mL 2-neck flask containing the partially fluorinated TEG bis chloroformate-Capstone 62-AL intermediate and the YMerOH-triol solution was transferred via cannula to the funnel. The YMerOH-triol solution was added to the 500 mL vessel in a slow continuous stream until all the YMerOH-triol was added. The mixture was allowed to stir at 50° C. under $N_2$ for 48 h. The reaction generated a large quantity of white pyridine salts which precipitated during the reaction. All additions and transfers were conducted under a dry $N_2$ atmosphere to avoid any contact with air.

The purification involved vacuum filtration of the pyridine salts using a Whatman 4 filter paper followed by rotary evaporation of the toluene. The product was treated with 1N HCl and extracted in dichloromethane-water mixture to remove excess pyridine, then neutralized with 1 N NaOH solution. The bottom organic layer was collected, washed twice with distilled water, and then rotary evaporated. The crude product (viscous oil) was incubated in a 250 mL round bottom flask with 100 mL distilled water for 48 h at 37° C. with gentle shaking to remove unreacted YMerOH-triol. The aqueous milky top layer was decanted off and the bottom oil was purified three times in 20% ethyl acetate/hexanes mixture. The procedure involved dissolution of the oil in ethyl acetate followed by precipitation in cold hexanes. This procedure removed the lower molecular weight byproducts which are the di- and mono-fluorinated derivatives of TEG-bischloroformate and fluoroalcohol reaction.

The purified product was dried at 75° C. and 4 mbar to yield a viscous clear oil (42% yield). The purified product was characterized by GPC (molecular weight based on polystyrene standards), and elemental analysis for fluorine. The average molecular weight (polystyrene equivalent) was 4018 g/mol. Polydispersity=1.24. Elemental analysis shows % F=15%. Thermal decomposition temperature (TGA, under $N_2$), at first onset: 223° C. (at 5% wt. loss). The chemical structure of compound 1 (YMerOH-1226-PCT-PC) is shown in FIG. 1.

Synthesis of Compound 2

All glassware used for the synthesis was dried in an oven at 110° C. overnight.

To a 200 mL 2-neck oven-dried flask equipped with a stir bar was added 50 g (0.048 mol) YMer diol (MW=1000 Da) and degassed overnight with gentle stirring at 60° C. Then, the YMer diol was purged with dry $N_2$, 53 mL of anhydrous chloroform ($CHCl_3$) were added to the flask using a cannula, followed by 15 g of anhydrous pyridine. The reaction mixture was stirred to dissolve the reagents and obtain a homogeneous solution. To a 1 L, 2-neck oven-dried flask equipped with a stir bar was added 60.9 g (0.221 mol) triethylene glycol (TEG) bis chloroformate. The flask was degassed for 15 min and then purged with dry $N_2$. After purging, 157 mL of anhydrous $CHCl_3$ were transferred into the flask by means of a cannula. The TEG bis chloroformate was stirred to dissolve in the solvent. To a 500 mL 2-neck flask was added 73.59 g (0.202 mol) of Capstone 62-AL fluoroalcohol (1H,1H,2H,2H-perfluoro-1-octanol), then degassed for 15 min and purged with dry $N_2$. To this was added 314 mL of anhydrous $CHCl_3$ followed by 28 g of pyridine. The flask was stirred to dissolve all the reagents. The Capstone 62-AL fluoroalcohol solution was transferred to a 500 mL addition funnel that was previously degassed and purged with $N_2$ using a cannula. The addition funnel was attached to the 1 L reaction vessel containing the TEG bis chloroformate solution that was cooled in an ice bath. The addition of the fluoroalcohol was done dropwise under $N_2$ for 1 h. Stirring was kept to a minimum during the reaction to form a partially fluorinated TEG bis chloroformate-Capstone 62-AL fluoroalcohol intermediate. Next, the YMer diol solution was transferred to the 1 L reaction vessel using a 20 gauge cannula in a slow continuous stream while the reaction vessel was cooled under an ice bath until all of the YMer diol solution had been added. The ice bath was removed and the reaction was allowed to proceed at room temperature for additional 10 min. The temperature was then raised to 50° C. and the reaction was allowed to run overnight. All additions and transfers were conducted under a dry $N_2$ atmosphere to avoid any contact with air.

Figure 2:
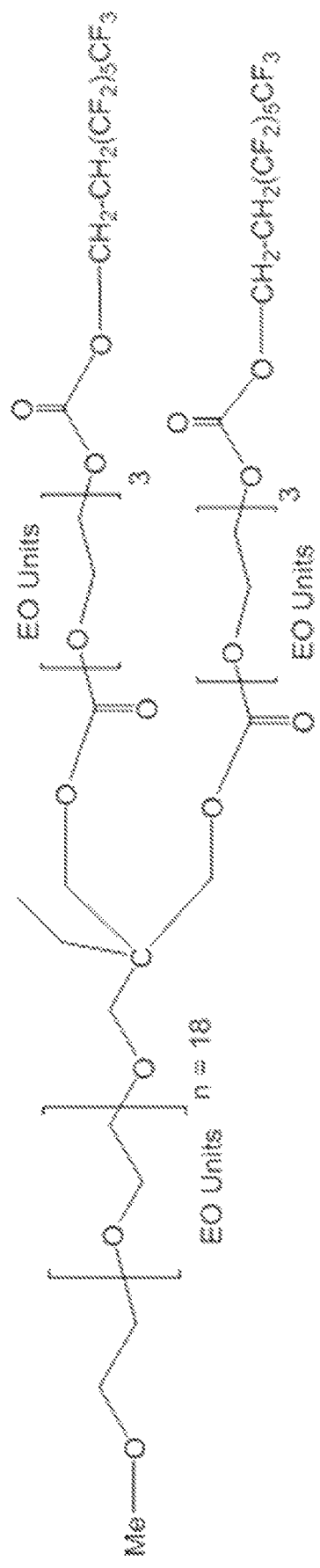
FIG. 2 shows the structure of compound (2).

The crude product was purified by first removing the $CHCl_3$ solvent on a rotary evaporator, dissolving the crude product in minimum THF, and cooling with ice bath for 20 min to precipitate the pyridine salts. The solution was vacuum filtered and the THF was evaporated using a rotary evaporator. The product was treated with 1N HCl and extracted in dichloromethane-water mixture to remove excess pyridine, then neutralized with 1N NaOH solution. The bottom organic layer was collected, washed twice with distilled water, and then rotary evaporated. Finally, the product was dissolved in minimum isopropyl alcohol (IPA), precipitated out in hexanes, washed 2× with hexanes, and dried under vacuum. The product was dried overnight at 60° C. in a vacuum oven to yield the product as a viscous liquid (59% yield). The purified product was characterized by GPC (molecular weight based on polystyrene standards), and elemental analysis for fluorine. The average molecular weight (polystyrene equivalent) was 3422 g/mol. Polydispersity=1.15. Elemental analysis: F=19%). Thermal decomposition temperature (TGA, under $N_2$), at first onset: 203° C. (at 5% wt loss). The chemical structure of compound 2 (YMer-1226-PCT-PC) is shown in FIG. 2.

Synthesis of Compound 3

All glassware used for the synthesis was dried in an oven at 110° C. overnight.

To a 200 mL 2-neck flask equipped with a stir bar was added 12 g (0.016 mol) of XMer tetraol (MW=771 Da), degassed overnight with gentle stirring at 60° C., and then purged with $N_2$ To a 500 mL 2-neck oven-dried flask equipped with a stir bar was added 9 g (0.033 mol) triethylene glycol (TEG) bis chloroformate. The flask was degassed for 15 min and then purged with dry $N_2$. After purging, 65 mL of anhydrous $CHCl_3$ was transferred into the flask by means of a syringe. The TEG bis chloroformate was stirred to dissolve in the solvent. To a 50 mL addition funnel was added 15 g (0.033 mol) of Capstone 62-AL fluoroalcohol (1H,1H,2H,2H-perfluoro-1-octanol), and degassed for 15 min and purged with dry $N_2$. To this addition funnel was added 20 mL of anhydrous $CHCl_3$ followed by 3 g of anhydrous pyridine, and the flask shaken to dissolve all reagents. The addition funnel was attached to the 500 mL reaction flask which was cooled in ice and dropwise addition of Capstone 62-AL fluoroalcohol to the TEG bis chloroformate was performed. The addition took 1 h to complete, and the reaction was allowed to proceed for additional 10 min at room temperature (25° C.) under $N_2$ atmosphere to form a partially fluorinated TEG bis chloroformate-Capstone 62-AL intermediate. While the partial fluorination was in progress, anhydrous $CHCl_3$ (122 mL) was added to the flask containing the XMer tetraol via a cannula, followed by 2.5 g of anhydrous pyridine, and the mixture was stirred to dissolve the reagents. Next, the X-Mer tetraol solution was transferred to the 500 mL reaction vessel using a 20 gauge cannula in a slow continuous stream while the reaction vessel was cooled in an ice bath until all of the XMer diol solution had been added. The ice bath was removed and the reaction was allowed to proceed at room temperature for additional 10 min. The temperature was then raised to 50° C. and the reaction was allowed to run overnight. All additions and transfers were conducted under a dry $N_2$ atmosphere to avoid any contact with air.

The purification involved rotary evaporation of $CHCl_3$ from the reaction mixture, addition of THF, and separation of the pyridine salts by vacuum filtration. The product was treated with 1N HCl and extracted in dichloromethane-water mixture to remove excess pyridine, then neutralized with 1N NaOH solution. The bottom organic layer was collected, further washed twice with distilled water and then rotary evaporated. Finally, the product was dissolved in minimum isopropyl alcohol (IPA), precipitated out in hexanes, washed 2× with hexanes, and dried under vacuum. The product was dried overnight at 60° C. in a vacuum oven to yield the product as a viscous liquid (59% yield).

Figure 3:
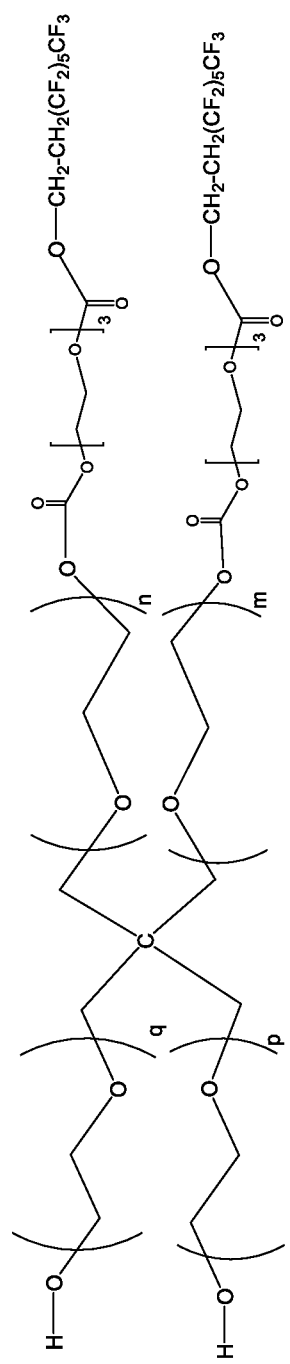
FIG. 3 shows the structure of compound (3).

The purified product was characterized by GPC (molecular weight based on polystyrene standards), and elemental analysis for fluorine. The average molecular weight (polystyrene equivalent) was 2322 g/mol. Polydispersity=1.12. Elemental analysis shows F=25.8% Thermal decomposition temperature (TGA, under $N_2$), at first onset: 221° C. (at 10 wt % loss). The chemical structure of compound 3 (XMer-1226-PCT-PC) is shown in FIG. 3.

Synthesis of Compound 4

All glassware used for the synthesis was dried in an oven at 110° C. overnight.

To a 100 mL 2-neck oven-dried flask equipped with a stir bar was added 15 g (0.008 mol) of PDP diol (MW=2000 Da), and degassed overnight with gentle stirring at 60° C. Then the PDP diol was purged with dry $N_2$, 90 mL of anhydrous $CHCl_3$ were transferred into the flask using a cannula, followed by 2 g of anhydrous pyridine. The reaction mixture was stirred to dissolve and obtain a homogeneous solution. To a 50 mL oven-dried addition funnel was added 5.63 g (0.016 mol) of bisphenol A chloroformate, the funnel was degassed for 15 min and then purged with dry $N_2$. After purging, 45 mL of anhydrous $CHCl_3$ were transferred into the funnel by means of a cannula. The funnel was shaken to dissolve the chloroformate. The addition funnel was attached to the flask containing the PDP diol and dropwise addition of bisphenol A chloroformate was performed over a period of 1 h at room temperature. The reaction was allowed to proceed for 3 h, allowing the formation of a PDP-bisphenol A prepolymer intermediate. While the prepolymer intermediate reaction was run, 7 g (0.019 mol) of Capstone 62-AL fluoroalcohol was added to a 50 mL 2-neck flask. The flask was degassed for 15 min and then purged under dry $N_2$. After purging with $N_2$, 15 mL of anhydrous $CHCl_3$ was added to the flask, followed by 2 g of anhydrous pyridine. The flask was shaken to dissolve the fluoroalcohol, which was then added to the 200 mL flask containing the prepolymer intermediate using a cannula in a slow continuous stream. The temperature was raised to 60° C. and the final end-capping reaction was allowed to proceed overnight. The product was purified by pouring the $CHCl_3$ reaction mixture into a separatory funnel containing deionized water, and the aqueous layer was acidified with 5 N HCl to neutralize any residual pyridine.

Figure 4:
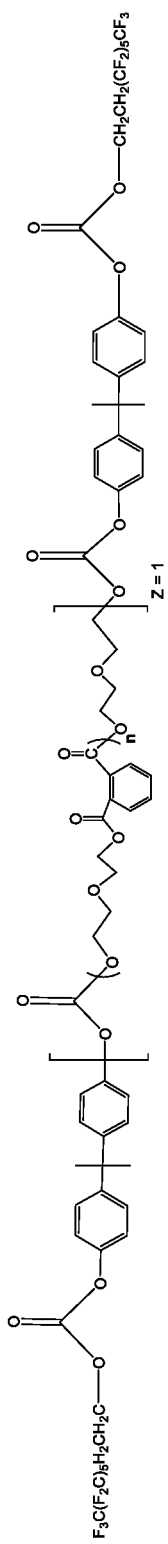
FIG. 4 shows the structure of compound (4).
Figure 5:
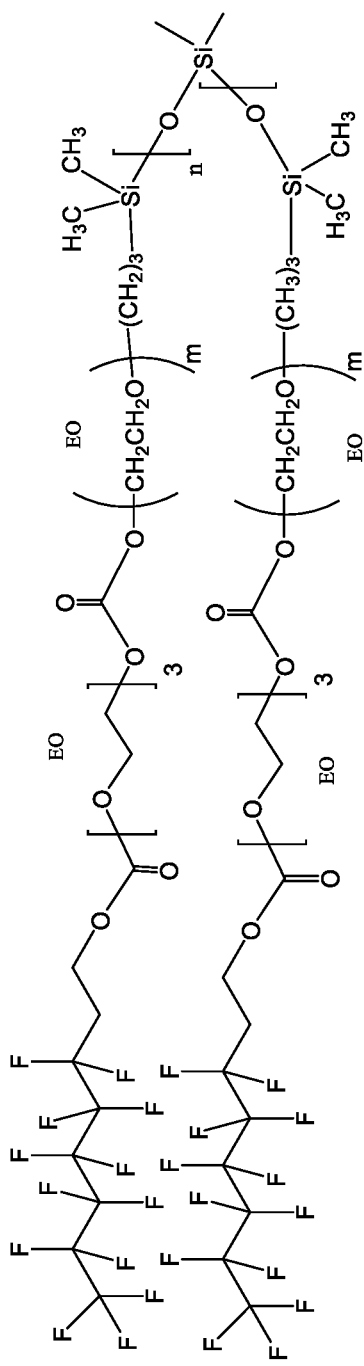
FIG. 5 shows the structure of compound (5).
Figure 6:
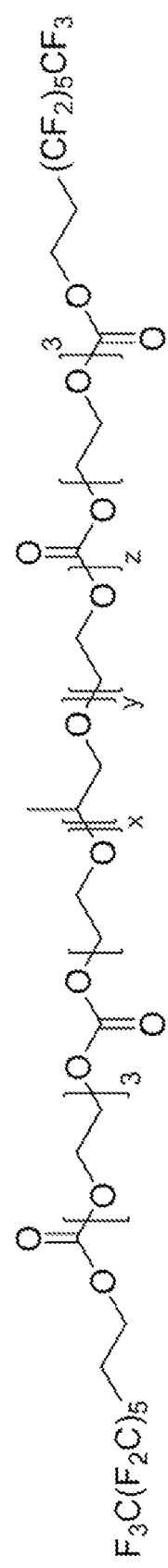
FIG. 6 shows the structure of compound (6).
Figure 7:
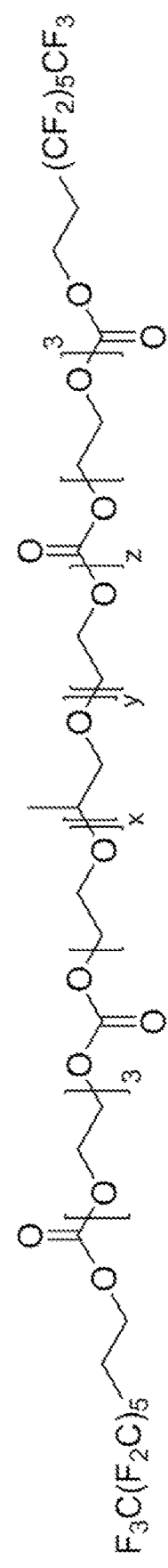
FIG. 7 shows the structure of compound (7).
Figure 8:
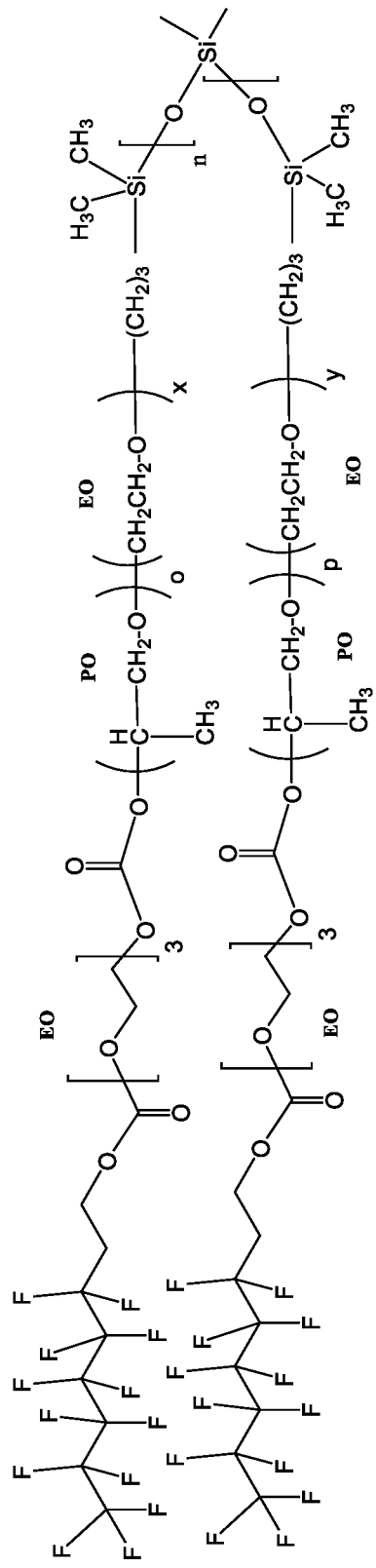
FIG. 8 shows the structure of compound (8).
Figure 9:
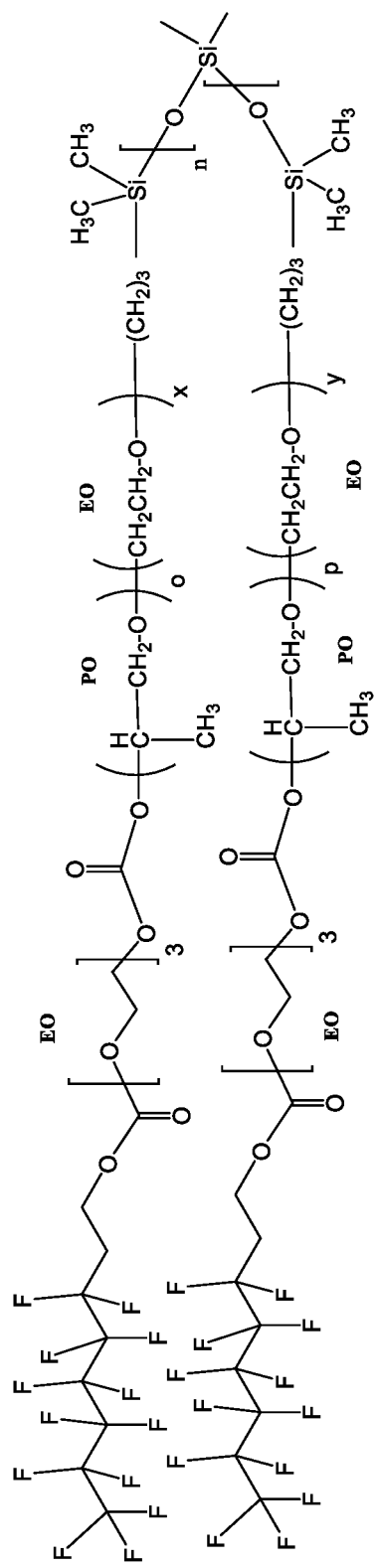
FIG. 9 shows the structure of compound (9).

The product was extracted into the organic layer neutralized with 1N NaOH solution and washed 2× with deionized water. The organic layer was dried over anhydrous $Na_2SO_4$. The solvent was removed on a rotary evaporator, the solid residue was dissolved in THF, and precipitated in a 3:1 water/methanol mixture. The product was dried in a vacuum oven (30 mbar) for 2 days to yield a solid. The purified product was characterized by GPC (molecular weight based on polystyrene standards). The average molecular weight (polystyrene equivalent) was 20704 g/mol. Polydispersity=1.52. Elemental analysis showed 4.20 wt % F, Thermal decomposition temperature (TGA, under $N_2$), at first onset: 314° C. (at 5 wt % loss). The chemical structure of compound 4 (PDP-1226-PCT-PC) is shown in FIG. 4.

Measurement of Immobilization and/or Denaturation of a Biologic on the Surface

The capability of the surface of an article of the invention reducing or preventing immobilization of a biologic can be compared to that of the surface of an article made from the same base polymer but lacking a surface modifying macromolecule. In a non-limiting example, a vessel prepared from an admixture of a base polymer and a surface modifying macromolecule ("Vessel") can be charged with a solution (e.g., aqueous solution) of a biologic (e.g., interferon β, a monoclonal antibody, a fusion protein (e.g., abatacept), an siRNA, or DNA (e.g., plasmid)) of predetermined concentration. Vessel can then be sealed, e.g., under inert atmosphere (e.g., under Ar or $N_2$). After storage of the biologic solution inside sealed Vessel for a period of time (e.g., 1 day, 3 days, 1 week, 2 weeks, 3 weeks, 1 month, 2 months, 3 months, 0.5 years, 0.75 years, 1 year, etc.) at room temperature or at a lower temperature (e.g., at 4° C. or at 0° C.) under ambient light (e.g., fluorescent light) or in the dark, the solution stored inside Vessel can be assessed for the total protein or nucleic acid concentration (e.g., using UV-Vis spectrometry or particle analyzer as known in the art). The change in the concentration of the biologic over time inside Vessel can then be compared to the change in the concentration of the biologic over time inside a vessel lacking a surface modifying macromolecule ("Control Vessel"). The magnitude of the decrease of the biologic concentration in Vessel can be at least 5% lower (e.g., at least 10% lower, at least 20% lower, at least 30% lower, at least 40% lower, or at least 50% lower) than that of the biologic concentration in Control Vessel over the same period of time, provided that the solutions were stored at the same temperature and light conditions.

OTHER EMBODIMENTS

Various modifications and variations of the described materials and methods of use of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A compound of formula (I):

$$F_T—OC(O)O—B—OC(O)O—[A—OC(O)O—B]_n—OC(O)O—F_T, \quad (I)$$

wherein
 (i) A comprises a soft segment and is covalently bound to B via a carbonate linkage;
 (ii) B comprises a polyalkylene oxide or a moiety described by the formula:

[chemical structure: bisphenol A moiety with two phenyl rings connected by C(CH$_3$)$_2$]

and is covalently bound to A via a carbonate linkage; and
 (iii) $F_T$ is a surface active group comprising a polyfluoroorgano group, wherein $F_T$ is covalently bound to B via a carbonate linkage; and
 (iv) n is an integer from 1 to 10.

2. The compound of claim 1, wherein B comprises polypropylene oxide, polyethylene oxide, or polytetramethylene oxide.

3. The compound of claim 1, wherein B is formed from triethylene glycol, tetraethylene glycol, or bisphenol A.

4. The compound of claim 1, wherein A comprises hydrogenated polybutadiene (HLBH), hydrogenated polyisoprene (HHTPI), poly ((2,2-dimethyl)-1,3-propylene carbonate), polybutadiene, poly (diethylene glycol)adipate (PEGA), poly (hexamethylene carbonate) (PHCN), poly (ethylene-co-butylene), (diethylene glycol-ortho phthalic anhydride) polyester, (1,6-hexanediol-ortho phthalic anhydride) polyester, (neopentyl glycol-ortho phthalic anhydride) polyester (PDP), a polysiloxane, bisphenol A ethoxylate, poly(ethylene oxide)-b-poly(propylene oxide)-b-poly(ethylene oxide) (PLN), polyethylene oxide (PEO), polypropylene oxide (PPO), or polytetramethylene oxide (PTMO).

5. The compound of claim 1, wherein the compound of formula (I) is further described by formula (II):

$$F_T—OC(O)O—(CH_2CH_2O)_m—OC(O)O—[A—OC(O)O—(CH_2CH_2O)_m]_n—OC(O)O—F_T \quad (II)$$

wherein
 (i) A comprises a soft segment;
 (ii) $F_T$ is a surface active group comprising a polyfluoroorgano group;
 (iii) m is an integer from 2 to 4; and
 (iv) n is an integer from 1 to 10.

6. The compound of claim 5, wherein A comprises hydrogenated polybutadiene (HLBH), hydrogenated polyisoprene (HHTPI), poly ((2,2-dimethyl)-1,3-propylene carbonate), polybutadiene, poly (diethylene glycol)adipate (PEGA), poly (hexamethylene carbonate) (PHCN), poly (ethylene-co-butylene), (diethylene glycol-ortho phthalic anhydride) polyester (PDP), (1,6-hexanediol-ortho phthalic anhydride) polyester, (neopentyl glycol-ortho phthalic anhydride) polyester, a polysiloxane, bisphenol A ethoxylate, poly(ethylene oxide)-b-poly(propylene oxide)-b-poly(ethylene oxide) (PLN), polyethylene oxide (PEO), polypropylene oxide (PPO), or polytetramethylene oxide (PTMO).

7. The compound of claim 6, wherein A comprises a triblock copolymer PPO-b-PEO-b-(polysiloxane)-b-PEO-b-PPO (PLNSi).

8. The compound of claim 6, wherein A comprises hydrogenated polyisoprene (HHTPI) or hydrogenated polybutadiene (HLBH).

9. The compound of claim 6, wherein A comprises polypropylene oxide (PPO) or polytetramethylene oxide (PTMO).

10. The compound of claim 6, wherein A comprises polyethylene oxide-polydimethylsiloxane-polyethylene oxide ($MW_{PEO}$=2,500 Da), polyethylene oxide-polydimethylsiloxane-polyethylene oxide ($MW_{PEO}$=1,000 Da), or polyethylene oxide-polydimethylsiloxane-polyethylene oxide ($MW_{PEO}$=2,500 Da).

11. The compound of claim 6, wherein A comprises propylene oxide-polydimethylsiloxane-propylene oxide block copolymer (C22 $MW_{PPO}$=2,500 Da).

12. The compound of claim 6,
 wherein A comprises polyethylene oxide (PEO); or
 wherein A comprises diethylene glycol-ortho phthalic anhydride; or
 wherein A comprises poly(ethylene oxide)-b-poly(propylene oxide)-b-poly(ethylene oxide) (PLN).

13. The compound of claim 1, wherein A is free of ester linkages.

14. The compound of claim 5, wherein A comprises hydrogenated polybutadiene (HLBH), hydrogenated polyisoprene (HHTPI), poly((2,2-dimethyl)-1,3-propylene carbonate), polybutadiene, poly(ethylene-co-butylene), a polysiloxane, bisphenol A ethoxylate, poly(ethylene oxide)-b-poly(propylene oxide)-b-poly(ethylene oxide) (PLN), polyethylene oxide (PEO), polypropylene oxide (PPO), or polytetramethylene oxide (PTMO).

15. A compound of formula (III):

[chemical structure (III): 
$F_T—O—C(=O)—O—B—O—C(=O)—O—$ connected to $X_1$ branch
$F_T—O—C(=O)—O—B—O—C(=O)—O—$ connected through $—O—[—O—]_n—O—X_2$]

wherein:
 (i) $F_T$ is a polyfluoroorgano group;
 (ii) each of $X_1$ and $X_2$ is, independently, is H, $CH_3$, or $CH_2CH_3$;
 (iii) B comprises a polyalkylene oxide; and
 (v) n is an integer from 5 to 100.

16. The compound of claim 15, wherein B comprises polypropylene oxide, polyethylene oxide, or polytetramethylene oxide.

17. The compound of claim 16, wherein B is formed from triethylene glycol or tetraethylene glycol.

18. The compound of claim 15,
wherein B is polyethylene oxide, $X_1$ is ethyl, and $X_2$ is H; or
wherein B is polyethylene oxide, $X_1$ is ethyl, and $X_2$ is methyl (YMer-1226-PCT-PC).

19. A compound of formula (IV):

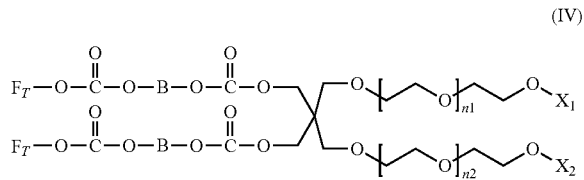

(IV)

wherein:

(i) each $F_T$ is a polyfluoroorgano;

(ii) each of $X_1$ and $X_2$ is, independently, H, $CH_3$, or $CH_2CH_3$;

(iii) B comprises a polyalkylene oxide; and (iv) each of n1 and n2 is independently an integer from 5 to 50.

20. The compound of claim 19, wherein B comprises polypropylene oxide, polyethylene oxide, or polytetramethylene oxide.

21. The compound of claim 20, wherein B is formed from triethylene glycol or tetraethylene glycol.

22. The compound of claim 19, wherein B is polyethylene oxide, $X_1$ is H, and $X_2$ is H.

* * * * *